(12) United States Patent
De Haro Garcia et al.

(10) Patent No.: US 10,464,932 B2
(45) Date of Patent: Nov. 5, 2019

(54) IMINOTHIADIAZINANE DIOXIDE DERIVATIVES AS PLASMEPSIN V INHIBITORS

(71) Applicant: UCB Biopharma SPRL, Brussels (BE)

(72) Inventors: Teresa De Haro Garcia, Slough (GB); Martin Alexander Lowe, Slough (GB); Malcolm Maccoss, Seabrook Island, SC (US); Richard David Taylor, Slough (GB); Zhaoning Zhu, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 16/076,387

(22) PCT Filed: Feb. 22, 2017

(86) PCT No.: PCT/EP2017/054023
§ 371 (c)(1),
(2) Date: Aug. 8, 2018

(87) PCT Pub. No.: WO2017/144517
PCT Pub. Date: Aug. 31, 2017

(65) Prior Publication Data
US 2019/0040053 A1 Feb. 7, 2019

(30) Foreign Application Priority Data
Feb. 23, 2016 (GB) .................................. 1603104.9

(51) Int. Cl.
*C07D 417/10* (2006.01)
*C07D 417/14* (2006.01)
*A61P 33/06* (2006.01)

(52) U.S. Cl.
CPC ............ *C07D 417/10* (2013.01); *A61P 33/06* (2018.01); *C07D 417/14* (2013.01)

(58) Field of Classification Search
CPC ..... C07D 417/10; C07D 417/14; A61K 31/54
USPC ..................................................... 514/222.5
See application file for complete search history.

(56) References Cited

FOREIGN PATENT DOCUMENTS

| WO | WO2005058311 A1 | 6/2005 | |
|---|---|---|---|
| WO | WO2006065277 A2 | 6/2006 | |
| WO | WO2008103351 A2 | 8/2008 | |
| WO | WO 2011/044181 | 4/2011 | |
| WO | WO-2011044181 A1 * | 4/2011 | ............ A61K 31/00 |

OTHER PUBLICATIONS

International Search Report and Written Opinion dated Mar. 24, 2017 for International Application No. PCT/EP2017/054023, 10 pages.
Sleebs, Brad E. et al., "Transition State Mimetics of the Plasmodium Export Element are Potent Inhibitors of Plasmepsin V from P. falciparum and P. vivax," Journal of Medicinal Chemistry, vol. 57, No. 18, Sep. 25, 2014, pp. 7644-7662.
I. Russo et al, I. Russo et al, Nature, 2010, pp. 632-636, vol. 463.

* cited by examiner

*Primary Examiner* — Kahsay Habte
(74) *Attorney, Agent, or Firm* — McDonnell Boehnen Hulbert & Berghoff LLP

(57) ABSTRACT

A series of 3-imino-5-methyl-1,2,4-thiadiazinane 1,1-dioxide derivatives of formula (I), substituted in the 5-position by a phenyl moiety NH which in turn is meta-substituted by an optionally substituted fused bicyclic heteroaromatic ring system containing at least one nitrogen atom, being selective inhibitors of plasmepsin V activity, are beneficial as pharmaceutical agents, especially in the treatment of malaria.

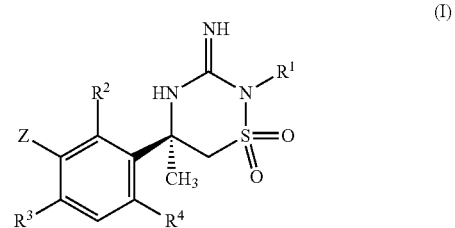

(I)

15 Claims, No Drawings

IMINOTHIADIAZINANE DIOXIDE DERIVATIVES AS PLASMEPSIN V INHIBITORS

This application is a national stage application under 35 U.S.C. § 371 of International Application No. PCT/EP2017/054023, filed Feb. 22, 2017, which claims the benefit of priority of United Kingdom Patent Application No. 1603104.9, filed Feb. 23, 2016.

The present invention relates to a class of heterocyclic compounds, and to their use in therapy. More particularly, this invention is concerned with pharmacologically active substituted iminothiadiazinane dioxide derivatives. These compounds are potent and selective inhibitors of plasmepsin V activity, and are accordingly of benefit as pharmaceutical agents, especially in the treatment of malaria.

Malaria is a mosquito-borne infectious disease, caused by a parasite of the genus *Plasmodium*, which has devastating consequences. In 2010, an estimated 225 million cases were reported, with 610,000 to 971,000 deaths, approximately 80% of which occurred in sub-Saharan Africa, mostly in young children (aged 5 years or less).

The aspartyl protease, plasmepsin V, is reported to be essential for the viability of the *Plasmodium falciparum* parasite and has accordingly been proposed as representing an attractive target enzyme for the discovery of antimalarial medicines (cf. I. Russo et al., *Nature*, 2010, 463, 632-636; and B. E. Sleebs et al., *J. Med. Chem.*, 2014, 57, 7644-7662).

The compounds in accordance with the present invention, being potent and selective inhibitors of plasmepsin V activity, are therefore beneficial in the treatment of malaria.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2008/103351, WO 2006/065277 and WO 2005/058311 describe a family of heterocyclic compounds that are stated to be aspartyl protease inhibitors. The compounds described in those publications are also stated to be effective in a method of inhibiting inter alia plasmepsins (specifically plasmepsins I and II) for treatment of malaria. However, there is no explicit suggestion in any of those publications that the compounds described therein might be effective in a method of inhibiting plasmepsin V activity.

The present invention provides a compound of formula (I) or a pharmaceutically acceptable salt thereof:

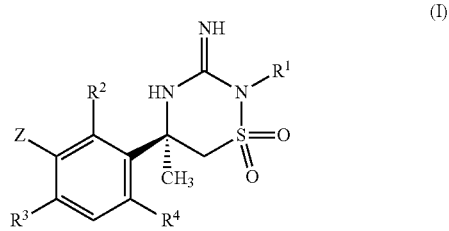

(I)

wherein

Z represents a fused bicyclic heteroaromatic ring system comprising ring A and ring B, in which ring A is an unsaturated five- or six-membered ring that is directly attached to the benzene ring depicted in formula (I) above;

ring A contains at least one nitrogen atom;

ring B is an unsaturated five- or six-membered ring that is fused to ring A;

the fused bicyclic heteroaromatic ring system Z optionally contains one, two or three additional heteroatoms selected from nitrogen, oxygen and sulfur, of which not more than one is an oxygen atom or a sulfur atom; and the fused bicyclic heteroaromatic ring system Z is optionally substituted by one or more substituents;

$R^1$ represents $C_{1-6}$ alkyl; and $R^2$, $R^3$ and $R^4$ independently represent hydrogen or halogen.

The compounds in accordance with the present invention are encompassed within the broadest generic scope of WO 2008/103351, WO 2006/065277 and WO 2005/058311. There is, however, no specific disclosure in any of those publications of a compound of formula (I) as defined above, or a pharmaceutically acceptable salt thereof.

The present invention also provides a compound of formula (I) as defined above, or a pharmaceutically acceptable salt thereof, for use in therapy.

The present invention also provides a compound of formula (I) as defined above, or a pharmaceutically acceptable salt thereof, for use in the treatment and/or prevention of malaria.

The present invention also provides a method for the treatment and/or prevention of malaria which comprises administering to a patient in need of such treatment an effective amount of a compound of formula (I) as defined above, or a pharmaceutically acceptable salt thereof.

The present invention also provides the use of a compound of formula (I) as defined above, or a pharmaceutically acceptable salt thereof, for the manufacture of a medicament for the treatment and/or prevention of malaria.

Where any of the groups in the compounds of formula (I) above is stated to be optionally substituted, this group may be unsubstituted, or substituted by one or more substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulfonyl" and "$C_{1-6}$ alkylamino" are to be construed accordingly.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulfur and nitrogen. Suitable heteroaryl groups include furyl, benzofuryl, dibenzofuryl, thienyl, benzothienyl, thieno[2,3-c]pyrazolyl, thieno[3,2-c]pyridinyl, dibenzothienyl, pyrrolyl, indolyl, pyrrolo[2,3-b]

pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

The absolute stereochemical configuration of the chiral carbon atom in the iminothiadiazinane dioxide nucleus of the compounds according to the invention is as depicted in formula (I) above. Generally, the compounds in accordance with the invention are at least 51% enantiomerically pure (by which it is meant that a sample thereof comprises a mixture of enantiomers containing 51% or more of the enantiomer depicted in formula (I) and 49% or less of the opposite antipode). Typically, the compounds in accordance with the invention are at least 60% enantiomerically pure. Appositely, the compounds in accordance with the invention are at least 75% enantiomerically pure. Suitably, the compounds in accordance with the invention are at least 80% enantiomerically pure. More suitably, the compounds in accordance with the invention are at least 85% enantiomerically pure. Still more suitably, the compounds in accordance with the invention are at least 90% enantiomerically pure. Even more suitably, the compounds in accordance with the invention are at least 95% enantiomerically pure. Preferably, the compounds in accordance with the invention are at least 99% enantiomerically pure. Ideally, the compounds in accordance with the invention are at least 99.9% enantiomerically pure.

Where the compounds of formula (I) have one or more additional asymmetric centres, they may accordingly exist as enantiomers. Where the compounds of use in the invention possess one or more additional asymmetric centres, they may also exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers or imide ($NHC=NH$)↔aminoimine ($N=CNH_2$) tautomers. Formula (I) and the formulae depicted hereinafter are intended to represent all individual tautomers and all possible mixtures thereof, unless stated or shown otherwise. In addition, under certain circumstances, e.g. where $R^2$ represents fluoro, compounds of formula (I) may exist as atropisomers. Formula (I) and the formulae depicted hereinafter are intended to represent all individual atropisomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, ring A is an unsaturated five-membered ring. In a second embodiment, ring A is an unsaturated six-membered ring.

In a first embodiment, ring B is an unsaturated five-membered ring. In a second embodiment, ring B is an unsaturated six-membered ring.

Thus, the fused bicyclic heteroaromatic ring system Z may typically comprise a five-membered ring fused to a five-membered ring, or a six-membered ring fused to a five-membered ring, or a six-membered ring fused to a six-membered ring, any of which ring systems may be optionally substituted by one or more substituents. The fused bicyclic heteroaromatic ring system Z may suitably comprise a six-membered ring fused to a five-membered ring, or a six-membered ring fused to a six-membered ring, either of which ring systems may be optionally substituted by one or more substituents. In a first embodiment, the fused bicyclic heteroaromatic ring system Z comprises a five-membered ring fused to a five-membered ring, which heteroaromatic ring system may be optionally substituted by one or more substituents. In a second embodiment, the fused bicyclic heteroaromatic ring system Z comprises a six-membered ring fused to a five-membered ring, which heteroaromatic ring system may be optionally substituted by one or more substituents. In a third embodiment, the fused bicyclic heteroaromatic ring system Z comprises a six-membered ring fused to a six-membered ring, which heteroaromatic ring system may be optionally substituted by one or more substituents.

In a first embodiment, the fused bicyclic heteroaromatic ring system Z contains one nitrogen atom (in ring A) and no additional heteroatoms. In a second embodiment, the fused bicyclic heteroaromatic ring system Z contains one nitrogen atom (in ring A) and one additional heteroatom selected from nitrogen, oxygen and sulfur. In a third embodiment, the fused bicyclic heteroaromatic ring system Z contains one nitrogen atom (in ring A) and two additional heteroatoms selected from nitrogen, oxygen and sulfur, of which not more than one is an oxygen atom or a sulfur atom. In a fourth embodiment, the fused bicyclic heteroaromatic ring system Z contains one nitrogen atom (in ring A) and three additional heteroatoms selected from nitrogen, oxygen and sulfur, of which not more than one is an oxygen atom or a sulfur atom.

Typically, ring A represents a pyrrole, pyrazole, oxazole, isoxazole, thiazole, isothiazole, imidazole, oxadiazole, thiadiazole, triazole, pyridine, pyridazine, pyrimidine, pyrazine or triazine ring.

Appositely, ring A represents a pyrrole or imidazole ring.

Suitably, ring A represents an imidazole ring.

Typically, ring B represents a benzene, furan, thiophene, pyrrole, pyrazole, oxazole, isoxazole, thiazole, isothiazole, imidazole, oxadiazole, thiadiazole, triazole, pyridine, pyridazine, pyrimidine, pyrazine or triazine ring.

Suitably, ring B represents a benzene ring.

Typical values of the fused bicyclic heteroaromatic ring system Z include thieno[2,3-c]pyrazolyl, thieno[3,2-c]pyridinyl, indolyl, pyrrolo[2,3-b]pyridinyl, pyrrolo-[3,2-c]pyridinyl, pyrrolo[3,4-b]pyridinyl, pyrazolo[1,5-a]pyridinyl, pyrazolo[3,4-d]-pyrimidinyl, indazolyl, benzoxazolyl, benzothiazolyl, benzimidazolyl, imidazo[2,1-b]-thiazolyl, imidazo[1,2-a]pyridinyl, imidazo[4,5-b]pyridinyl, purinyl, imidazo[1,2-a]-pyrimidinyl, imidazo[1,2-a]pyrazinyl, [1,2, 4]triazolo[1,5-a]pyrimidinyl, benzotriazolyl, quinolinyl, isoquinolinyl, naphthyridinyl, cinnolinyl, phthalazinyl, quinazolinyl, quinoxalinyl and pteridinyl, any of which groups may be optionally substituted by one or more substituents.

Selected values of the fused bicyclic heteroaromatic ring system Z include indolyl and benzimidazolyl, either of which groups may be optionally substituted by one or more substituents.

Suitable values of the fused bicyclic heteroaromatic ring system Z include benzimidazolyl, which group may be optionally substituted by one or more substituents.

Typical values of optional substituents on Z include halogen, cyano, nitro, $C_{1-6}$ alkyl, trifluoromethyl, methylpyrazolyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl. Additional values include pyrrolidinyl and morpholinyl.

Selected values of optional substituents on Z include halogen, cyano, $C_{1-6}$ alkyl, trifluoromethyl, di($C_{1-6}$)alkylamino, pyrrolidinyl and morpholinyl.

Suitable values of optional substituents on Z include halogen, $C_{1-6}$ alkyl and trifluoromethyl.

Typical values of particular substituents on Z include fluoro, chloro, bromo, cyano, nitro, methyl, ethyl, isopropyl, trifluoromethyl, methylpyrazolyl, hydroxy, hydroxymethyl, hydroxyethyl, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl. Additional values include pyrrolidinyl and morpholinyl.

Selected values of particular substituents on Z include fluoro, chloro, cyano, methyl, trifluoromethyl, dimethylamino, pyrrolidinyl and morpholinyl.

Suitable values of particular substituents on Z include chloro, methyl and trifluoromethyl.

Typical values of Z include (chloro)(cyano)(methyl)indolyl, dimethylpyrazolo-[1,5-a]pyridinyl, chloroindazolyl, benzothiazolyl, chlorobenzimidazolyl, methyl-benzimidazolyl, (chloro)(methyl)benzimidazolyl, (bromo)(methyl)benzimidazolyl, (cyano)(methyl)benzimidazolyl, (chloro)(ethyl)benzimidazolyl, (methyl)(trifluoro-methyl)benzimidazolyl, (methyl)(methylpyrazolyl)benzimidazolyl, (chloro)-(hydroxymethyl)benzimidazolyl, (methoxy)(methyl)benzimidazolyl, (methyl)-(methylsulfonyl)benzimidazolyl, (carboxy)(methyl)benzimidazolyl, (dimethylamino-carbonyl)(methyl)benzimidazolyl, (dimethylaminosulfonyl)(methyl)benzimidazolyl, (dichloro)(methyl)benzimidazolyl, (chloro)(methyl)(trifluoromethyl)benzimidazolyl, imidazo[1,2-a]pyridinyl, (chloro)(methyl)imidazo[1,2-a]pyridinyl, (methyl)(methyl-pyrazolyl)imidazo[1,2-a]pyridinyl, (chloro)(methyl)imidazo[4,5-b]pyridinyl, dimethyl-imidazo[4,5-b]pyridinyl and quinolinyl. Additional values include (chloro)(dimethyl-amino)benzimidazolyl, (chloro)(pyrrolidinyl)benzimidazolyl, (chloro)(morpholinyl)-benzimidazolyl and (fluoro)(methyl)(trifluoromethyl)benzimidazolyl.

Selected values of Z include (chloro)(cyano)(methyl)indolyl, (chloro)(methyl)-benzimidazolyl, (chloro)(dimethylamino)benzimidazolyl, (chloro)(pyrrolidinyl)-benzimidazolyl, (chloro)(morpholinyl)benzimidazolyl, (fluoro)(methyl)(trifluoromethyl)-benzimidazolyl and (chloro)(methyl)(trifluoromethyl)benzimidazolyl.

Suitable values of Z include (chloro)(methyl)benzimidazolyl and (chloro)(methyl)-(trifluoromethyl)benzimidazolyl.

Typically, $R^1$ represents $C_{1-4}$ alkyl.

Particular values of $R^1$ include methyl, ethyl and isopropyl.

Suitably, $R^1$ represents methyl.

In one embodiment, $R^2$ represents hydrogen. In another embodiment, $R^2$ represents halogen, especially fluoro or chloro. In one aspect of that embodiment, $R^2$ represents fluoro. In another aspect of that embodiment, $R^2$ represents chloro.

In one embodiment, $R^3$ represents hydrogen. In another embodiment, $R^3$ represents halogen, especially fluoro or chloro. In one aspect of that embodiment, $R^3$ represents fluoro. In another aspect of that embodiment, $R^3$ represents chloro.

In one embodiment, $R^4$ represents hydrogen. In another embodiment, $R^4$ represents halogen, especially fluoro or chloro. In one aspect of that embodiment, $R^4$ represents fluoro. In another aspect of that embodiment, $R^4$ represents chloro.

In a first embodiment, $R^2$, $R^3$ and $R^4$ all represent hydrogen. In a second embodiment, $R^2$ represents halogen, and $R^3$ and $R^4$ both represent hydrogen. In a third embodiment, $R^2$ and $R^4$ both represent hydrogen, and $R^3$ represents halogen. In a fourth embodiment, $R^2$ and $R^3$ both represent halogen, and $R^4$ represents hydrogen. In a fifth embodiment, $R^2$ and $R^3$ both represent hydrogen, and $R^4$ represents halogen. In a sixth embodiment, $R^2$ and $R^4$ both represent halogen, and $R^3$ represents hydrogen. In a seventh embodiment, $R^2$ represents hydrogen, and $R^3$ and $R^4$ both represent halogen. In an eight embodiment, $R^2$, $R^3$ and $R^4$ all represent halogen.

Typically, $R^2$ represents hydrogen or halogen, and $R^3$ and $R^4$ both represent hydrogen.

One sub-class of compounds according to the invention is represented by the compounds of formula (IIA), and pharmaceutically acceptable salts thereof:

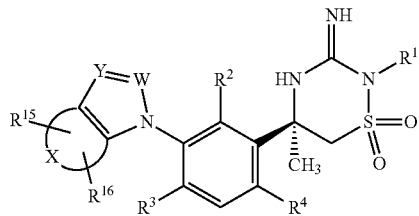

(IIA)

wherein

X represents the residue of a benzene or pyridine ring;

W represents N or C—$R^{13}$;

Y represents N or C—$R^{14}$;

$R^{13}$ represents hydrogen, methyl, ethyl, hydroxymethyl, 1-hydroxyethyl, dimethylamino, pyrrolidinyl or morpholinyl;

$R^{14}$ represents hydrogen, cyano or $C_{1-4}$ alkyl;

$R^{15}$ and $R^{16}$ independently represent hydrogen, halogen, cyano, nitro, $C_{1-6}$ alkyl, trifluoromethyl, methylpyrazolyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$) alkylaminosulfonyl; and $R^1$, $R^2$, $R^3$ and $R^4$ are as defined above.

As specified above, X represents the residue of a benzene or pyridine ring, by which it is meant that the integer X, when taken together with the two carbon atoms of the adjoining five-membered ring, represents a benzene or pyridine ring. In a first embodiment, X represents the residue of a benzene ring. In a second embodiment, X represents the residue of a pyridine ring.

In a first embodiment, W represents N. In a second embodiment, W represents C—$R^{13}$.

In a first embodiment, Y represents N. In a second embodiment, Y represents C—$R^{14}$.

Suitably, W represents C—$R^{13}$ and Y represents N; or W represents C—$R^{13}$ and Y represents C—$R^{14}$; or W represents N and Y represents C—$R^{14}$.

Appositely, W represents C—$R^{13}$ and Y represents N; or W represents C—$R^{13}$ and Y represents C—$R^{14}$.

In a first embodiment, W represents C—$R^{13}$ and Y represents N. In a second embodiment, W represents C—$R^{13}$ and Y represents C—$R^{14}$. In a third embodiment, W represents N and Y represents C—$R^{14}$.

Generally, $R^{13}$ represents hydrogen, methyl, ethyl, hydroxymethyl or 1-hydroxyethyl.

Suitably, $R^{13}$ represents methyl, dimethylamino, pyrrolidinyl or morpholinyl.

In a first embodiment, $R^{13}$ represents hydrogen. In a second embodiment, $R^{13}$ represents methyl. In a third embodiment, $R^{13}$ represents ethyl. In a fourth embodiment, $R^{13}$ represents hydroxymethyl. In a fifth embodiment, $R^{13}$ represents 1-hydroxyethyl. In a sixth embodiment, $R^{13}$ represents dimethylamino. In a seventh embodiment, $R^{13}$ represents pyrrolidinyl. In an eighth embodiment, $R^{13}$ represents morpholinyl.

In a first embodiment, $R^{14}$ represents hydrogen. In a second embodiment, $R^{14}$ represents cyano. In a third embodiment, $R^{14}$ represents $C_{1-4}$ alkyl, especially methyl.

Typically, $R^{15}$ and $R^{16}$ may independently represent hydrogen, fluoro, chloro, bromo, cyano, nitro, methyl, ethyl, isopropyl, trifluoromethyl, methylpyrazolyl, hydroxy, hydroxymethyl, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl or dimethylaminosulfonyl.

Typical values of $R^{15}$ include hydrogen, halogen and trifluoromethyl.

Suitable values of $R^{15}$ include hydrogen, fluoro, chloro and trifluoromethyl.

Selected values of $R^{15}$ include hydrogen, chloro and trifluoromethyl.

Typical values of $R^{16}$ include hydrogen and halogen.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro.

Selected values of $R^{16}$ include hydrogen, fluoro and chloro.

Suitable values of $R^{16}$ include hydrogen and chloro.

Particular subgroups of the compounds of formula (IIA) above are represented by the compounds of formula (IIA-1), (IIA-2) and (IIA-3), and pharmaceutically acceptable salts thereof:

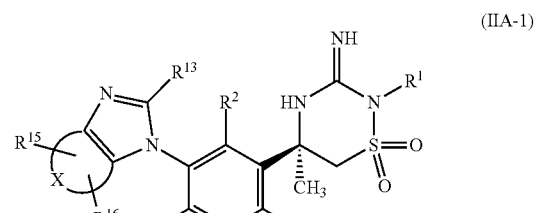

wherein X, $R^1$, $R^2$, $R^3$, $R^4$, $R^{13}$, $R^{14}$, $R^{15}$ and $R^{16}$ are as defined above.

Specific subgroups of the compounds of formula (IIA-1) above include the compounds of formula (IIA-1a), (IIA-1b) and (IIA-1c), and pharmaceutically acceptable salts thereof:

-continued (IIA-1c)

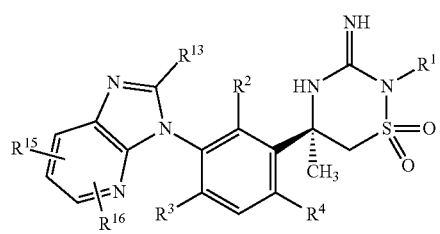

wherein $R^1$, $R^2$, $R^3$, $R^4$, $R^{13}$, $R^{15}$ and $R^{16}$ are as defined above.

A specific subgroup of the compounds of formula (IIA-2) above includes the compounds of formula (IIA-2a), and pharmaceutically acceptable salts thereof:

(IIA-2a)

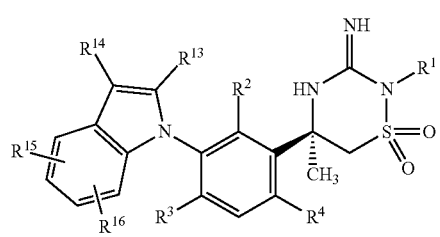

wherein $R^1$, $R^2$, $R^3$, $R^4$, $R^{13}$, $R^{14}$, $R^{15}$ and $R^{16}$ areas defined above.

A specific subgroup of the compounds of formula (IIA-3) above includes the compounds of formula (IIA-3a), and pharmaceutically acceptable salts thereof:

(IIA-3a)

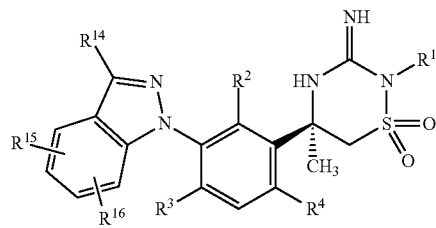

wherein $R^1$, $R^2$, $R^3$, $R^4$, $R^{14}$, $R^{15}$ and $R^{16}$ are as defined above.

Another sub-class of compounds according to the invention is represented by the compounds of formula (IIB), and pharmaceutically acceptable salts thereof:

(IIB)

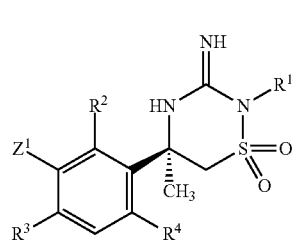

wherein
$Z^1$ represents a group of formula (Za), (Zb), (Zc) or (Zd):

(Za)

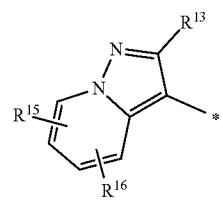

(Zb)

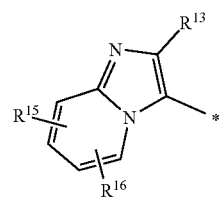

(Zc)

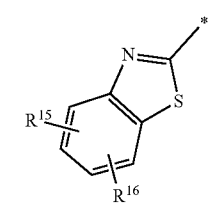

(Zd)

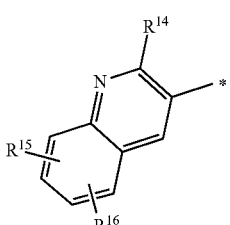

in which the asterisk (*) represents the point of attachment to the remainder of the molecule; and
$R^1$, $R^2$, $R^3$, $R^4$, $R^{13}$, $R^{14}$, $R^{15}$ and $R^{16}$ are as defined above.

In a first embodiment, $Z^1$ represents a group of formula (Za) as defined above. In a second embodiment, $Z^1$ represents a group of formula (Zb) as defined above. In a third embodiment, $Z^1$ represents a group of formula (Zc) as defined above. In a fourth embodiment, $Z^1$ represents a group of formula (Zd) as defined above.

Specific novel compounds in accordance with the present invention include each of the compounds whose preparation is described in the accompanying Examples, and pharmaceutically acceptable salts thereof.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

General methods for the preparation of the compounds of formula (I) as defined above are described in WO 2008/103351.

The compounds in accordance with the invention as represented by formula (IIA-1) above may be prepared by a process which comprises reacting a compound of formula $R^{13}$—CHO with a compound of formula (III):

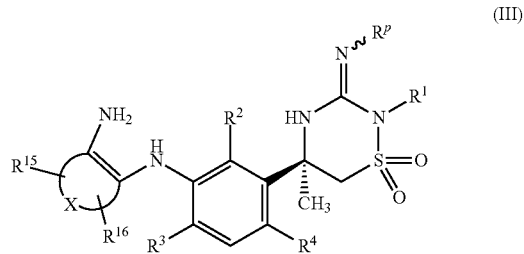

(III)

wherein X, $R^1$, $R^2$, $R^3$, $R^4$, $R^{13}$, $R^{15}$ and $R^{16}$ are as defined above, and $R^p$ represents hydrogen or an N-protecting group; in the presence of a transition metal catalyst; followed, as necessary, by removal of the N-protecting group $R^p$.

Suitably, the transition metal catalyst of use in the above reaction is a copper(II) salt, e.g. copper(II) acetate.

The reaction between the compound of formula $R^{13}$—CHO and compound (III) is conveniently accomplished at an elevated temperature in a suitable solvent, e.g. a $C_{1-4}$ alkanol such as ethanol.

In an alternative procedure, the compounds in accordance with the invention as represented by formula (IIA-1) above may be prepared by a process which comprises reacting a compound of formula $R^{13}$—$CO_2H$ with a compound of formula (III) as defined above; followed, as necessary, by removal of the N-protecting group $R^p$.

The reaction between the compound of formula $R^{13}$—$CO_2H$ and compound (III) is conveniently accomplished by mixing the reactants at an elevated temperature.

In an alternative procedure, the compounds in accordance with the invention as represented by formula (IIA-1) above, wherein $R^{13}$ represents dimethylamino, may be prepared by a process which comprises reacting (dichloromethylene)

dimethylammonium chloride (Vilsmeier reagent) with a compound of formula (III) as defined above; followed, as necessary, by removal of the N-protecting group $R^p$.

The reaction between Vilsmeier reagent and compound (III) is conveniently accomplished at ambient temperature in a suitable solvent, e.g. a chlorinated solvent such as dichloromethane.

Similarly, the compounds in accordance with the invention as represented by formula (IIA-1) above, wherein $R^{13}$ represents pyrrolidin-1-yl or morpholin-4-yl, may be prepared by a process which comprises reacting 1-(dichloromethylene)pyrrolidinium chloride or 4-(dichloromethylene)morpholin-4-ium chloride respectively with a compound of formula (III) as defined above; followed, as necessary, by removal of the N-protecting group $R^p$.

The reaction between 1-(dichloromethylene)pyrrolidinium chloride or 4-(dichloro-methylene)morpholin-4-ium chloride and compound (III) is conveniently accomplished at ambient temperature in a suitable solvent, e.g. a chlorinated solvent such as dichloromethane.

In an alternative procedure, the compounds in accordance with the invention as represented by formula (IIA-1) above, wherein $R^{13}$ represents pyrrolidin-1-yl or morpholin-4-yl, may be prepared by a three-step procedure which comprises: (i) reacting a compound of formula (III) as defined above with triphosgene; (ii) treatment of the resulting compound with phosphorus oxychloride; and (iii) treatment of the chloro derivative thereby obtained with pyrrolidine or morpholine respectively; including removal of the N-protecting group $R^p$, as necessary.

Step (i) will generally be accomplished in the presence of a base, e.g. an organic base such as trimethylamine. The reaction is conveniently effected at ambient temperature in a suitable solvent, e.g. a cyclic ether such as tetrahydrofuran.

Step (ii) is conveniently effected at an elevated temperature. Step (iii) is conveniently effected at an elevated temperature in a suitable solvent, e.g. a $C_{1-4}$ alkanol such as propan-2-ol.

Suitably, the N-protecting group $R^p$ is tert-butoxycarbonyl (BOC).

Where the N-protecting group $R^p$ is BOC, subsequent removal of the BOC group may suitably be accomplished by treatment with an acid, e.g. a mineral acid such as hydrochloric acid, or an organic acid such as trifluoroacetic acid, typically at ambient temperature in a suitable solvent, e.g. a chlorinated solvent such as dichloromethane, or a cyclic ether such as 1,4-dioxane.

The intermediates of formula (III) above may be prepared by treating a compound of formula (IV):

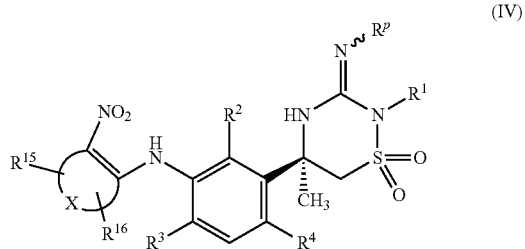

(IV)

wherein X, $R^1$, $R^2$, $R^3$, $R^4$, $R^{15}$, $R^{16}$ and $R^p$ are as defined above; with a reducing agent.

Suitably, the reducing agent of use in the above reaction may be a mixture of zinc and ammonium formate, in which case the reaction may conveniently be accomplished at ambient temperature in a suitable solvent, e.g. a $C_{1-4}$ alkanol such as methanol.

Alternatively, the reducing agent may be tin(II) chloride, in which case the reaction may conveniently be accomplished at an elevated temperature in a suitable solvent, e.g. a $C_{1-4}$ alkanol such as ethanol.

The intermediates of formula (IV) above may be prepared by reacting a compound of formula (V) with a compound of formula (VI):

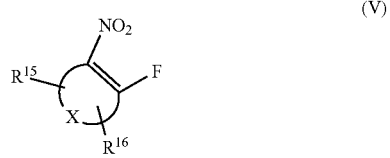

(V)

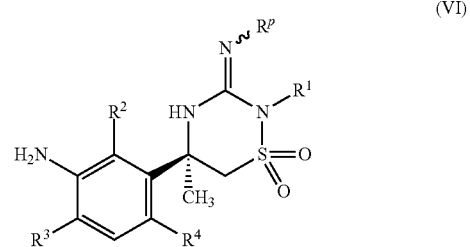

(VI)

wherein X, $R^1$, $R^2$, $R^3$, $R^4$, $R^5$, $R^{16}$ and $R^p$ are as defined above.

The reaction will generally be accomplished in the presence of a base, typically a strong organic base such as tert-butyllithium or lithium bis(trimethylsilyl)amide. The reaction may conveniently be effected in a suitable solvent, e.g. a cyclic ether such as tetrahydrofuran.

The compounds in accordance with the invention as represented by formula (IIA-2) above may be prepared by a two-step procedure which comprises: (i) reacting a compound of formula (VI) as defined above with a compound of formula (VII):

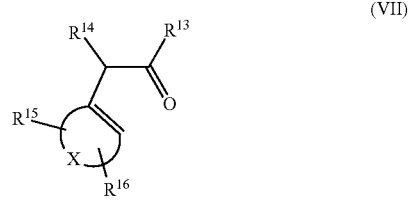

(VII)

wherein X, $R^1$, $R^{14}$, $R^{15}$ and $R^{16}$ are as defined above; and (ii) treatment of the resulting material with [bis(trifluoroacetoxy)iodo]benzene; followed, as necessary, by removal of the N-protecting group $R^p$.

Step (i) is conveniently effected at an elevated temperature in acetic acid.

Step (ii) is conveniently effected in a suitable solvent, e.g. a chlorinated solvent such as dichloromethane.

The compounds in accordance with the invention as represented by formula (IIA-3) above may be prepared by a process which comprises reacting a compound of formula (VIII) with a compound of formula (IX):

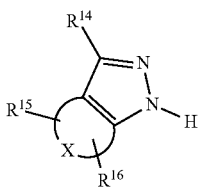

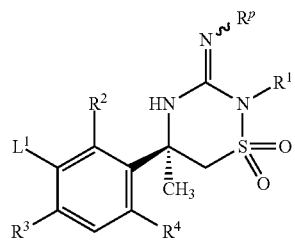

wherein X, $R^1$, $R^2$, $R^3$, $R^4$, $R^{14}$, $R^{15}$, $R^{16}$ and $R^p$ are as defined above, and $L^1$ represents a suitable leaving group; in the presence of a transition metal catalyst; followed, as necessary, by removal of the N-protecting group $R^p$.

The leaving group $L^1$ is typically a halogen atom, e.g. bromo.

Suitably, the transition metal catalyst of use in the above reaction is a copper(II) salt, e.g. copper(II) acetate.

The reaction is conveniently accomplished at an elevated temperature in a suitable solvent, e.g. a dipolar aprotic solvent such as N,N-dimethylformamide, typically in the presence of pyridine.

The compounds in accordance with the invention as represented by formula (IIB) above may be prepared by a process which comprises reacting a compound of formula $Z^1$-$L^2$ with a compound of formula (X):

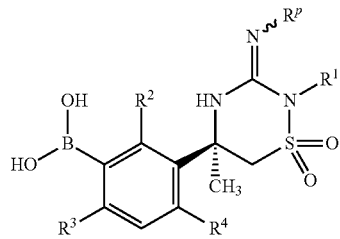

wherein $Z^1$, $R^1$, $R^2$, $R^3$, $R^4$ and $R^p$ are as defined above, and $L^2$ represents a suitable leaving group; in the presence of a transition metal catalyst; followed, as necessary, by removal of the N-protecting group $R^p$.

The leaving group $L^2$ is typically a halogen atom, e.g. bromo.

The transition metal catalyst of use in the reaction between the compound of formula $Z^1$-$L^2$ and compound (X) is suitably a palladium-containing catalyst such as chloro (2-dicyclohexylphosphino-2',4',6'-triisopropyl-1,1'-biphenyl)[2-(2'-amino-1,1'-biphenyl)]palladium(II).

The reaction is conveniently carried out at an elevated temperature in a suitable solvent, e.g. a $C_{1-4}$ alkanol such as ethanol, typically in the presence of 2-dicyclohexylphosphino-2',4',6'-triisopropylbiphenyl and a salt such as potassium acetate, potassium carbonate, potassium phosphate or sodium carbonate.

The intermediates of formula (X) above may be prepared by reacting a compound of formula (IX) as defined above with tetrahydroxydiboron; in the presence of a transition metal catalyst; under conditions analogous to those described above for the reaction between the compound of formula $Z^1$-$L^2$ and compound (X).

Where they are not commercially available, the starting materials of formula (V), (VI), (VII), (VIII) and (IX) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art.

By way of example, a compound of formula (I) wherein Z is substituted by halogen, e.g. bromo or chloro, may be converted into the corresponding compound wherein Z is substituted by 1-methylpyrazol-4-yl by treatment with 1-methylpyrazol-4-ylboronic acid or a cyclic ester thereof formed with an organic diol, e.g. pinacol, 1,3-propanediol or neopentyl glycol. The reaction is typically effected in the presence of a transition metal catalyst, e.g. a palladium-containing catalyst such as (2-dicyclohexylphosphino-2',4', 6'-triisopropylbiphenyl)palladium(II) phenethylamine chloride or chloro(2-dicyclohexylphosphino-2',4',6'-triisopropyl-1,1'-biphenyl)[2-(2'-amino-1,1'-biphenyl)] palladium(II), and a base, e.g. an inorganic base such as potassium tert-butoxide, potassium acetate or potassium carbonate.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds of the present invention are potent and selective inhibitors of plasmepsin V activity, inhibiting the aspartyl protease activity of *Plasmodium falciparum*: plasmepsin V ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective activity, typically at least a 20-fold selective activity, suitably at least a 50-fold selective activity, and ideally at least a 100-fold selective activity, for *Plasmodium falciparum* plasmepsin V relative to human aspartyl protease enzymes (including BACE).

Plasmepsin V Enzyme Assays

The assays used to measure the effect of test compounds on plasmepsin V activity were fluorescent resonant energy transfer (FRET) based, using a peptide substrate that had been labelled at each end with one of the FRET pair EDANS/Dabcyl. Excitation of EDANS results in fluorescent resonant energy transfer to Dabcyl, which is a dark quencher. Cleavage of the peptide by the protease prevents FRET with a resultant increase in EDANS fluorescent emission. Inhibition of the protease results in a decrease in the fluorescent signal. Test compounds were assayed in either one or the other of the two assays described below.

Plasmepsin V Assay 1

Plasmepsin V enzyme was diluted to 12.5 nM in assay buffer (50 mM sodium citrate, pH 6.5, 0.002% Tween 20). Test compounds were serially diluted 3-fold in DMSO (10 point titration), before being further diluted 1 in 10 in assay buffer. Plasmepsin V substrate (Anaspec catalogue number 64939) was dissolved in DMSO to 1 mM, before being further diluted 1 in 10 in assay buffer to 100 μM. Diluted test compound (5 μL) was mixed with plasmepsin V (40 μL) and incubated for 30 minutes at room temperature after addition of diluted plasmepsin V substrate (5 μL). The final concentrations of enzyme and substrate were 10 nM and 10 μM respectively. Final concentrations of test compound ranged from 100,000 nM to 5 nM in 2% DMSO. Fluorescent signal was measured using an Analyst HT plate reader (Excitation 330 nm, Emission 485 nm). Compound effect was expressed as % inhibition of the maximum signal generated (DMSO only controls) after subtraction of the minimum signal (no enzyme controls) from both. The $IC_{50}$ value was calculated from % inhibition, using a four parameter logistic curve fit.

Plasmepsin V Assay 2

Plasmepsin V enzyme was diluted to 40 nM in assay buffer (50 mM sodium citrate, pH 6.5, 0.002% Tween 20). Test compounds were serially diluted 2-fold in assay buffer (15 point titration). Plasmepsin V substrate (Anaspec catalogue number 64939) was dissolved in DMSO to 1 mM, before being further diluted 1 in 25 in assay buffer to 40 μM. Diluted test compound (12.5 μL) was mixed with plasmepsin V (6.25 μL) and incubated for 30 minutes at room temperature after addition of of diluted plasmepsin V substrate (6.25 μL). The final concentrations of enzyme and substrate were 10 nM and 10 μM respectively. Final top concentrations of test compound ranged from 5 μM to 30 μM in 1% DMSO. Fluorescent signal was measured using a SpectraMax Paradigm plate reader (Excitation 360 nm, Emission 465 nm). Fluorescence intensity of the samples with test compound was used to calculate the $IC_{50}$ value, using a four parameter logistic curve fit.

When tested in the plasmepsin V enzyme assay as described above (Assay 1 or Assay 2), the compounds of the accompanying Examples were all found to exhibit $IC_{50}$ values of 50 μM or better.

Thus, when tested in the plasmepsin V assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, appositely in the range of about 0.01 nM to about 500 nM, ideally in the range of about 0.01 nM to about 100 nM, and preferably in the range of about 0.01 nM to about 25 nM.

EXAMPLES

| Abbreviations | |
|---|---|
| DCM: dichloromethane | EtOAc: ethyl acetate |
| DMSO: dimethyl sulfoxide | THF: tetrahydrofuran |
| MeOH: methanol | EtOH: ethanol |
| TFA: trifluoroacetic acid | |
| h: hour | M: mass |
| DAD: Diode Array Detector | |
| HPLC: High Performance Liquid Chromatography | |
| LCMS: Liquid Chromatography Mass Spectrometry | |
| ES+: Electrospray Positive Ionisation | |

Nomenclature

Compounds were named with the aid of ACD/Name Batch (Network) version.

Analytical Conditions

LCMS data for all Examples were determined by using Method 1 below.

Method 1

| | |
|---|---|
| Column: | Waters x Bridge C18, 2.1 × 30 mm, 2.5 μm |
| Injection Volume | 5.0 μL |
| Flow Rate | 1.00 mL/minute |

Detection:

MS—ESI+m/z 150 to 800

UV—DAD 220-400 nm

| | |
|---|---|
| Solvent A | 5 mM ammonium formate in water + 0.1% ammonia |
| Solvent B | acetonitrile + 5% Solvent A + 0.1% ammonia |

Gradient Program:
 5% B to 95% B in 4.0 minutes; hold until 5.00 minutes; at 5.10 minutes concentration of B is 5%; hold up to 6.5 minutes

Intermediate 1

(NE)-N-[1-(2-Fluoro-3-nitrophenyl)ethylidene]-2-methylpropane-2-sulfinamide (R)-(+)-2-Methyl-2-propanesulfinamide (400 g, 3.28 mol), 1-(2-fluoro-3-nitro-phenyl)ethanone (500 g, 2.73 mol) and titanium(IV) ethoxide (1550 g, 8.4 mol) in THF (5.0 L) were stirred at 70° C. for 16 h. The mixture was washed with water and filtered. The filter cake was washed with ethyl acetate (15 L), then the filtrate was washed with brine (5 L) and dried over $Na_2SO_4$. The organic layer was concentrated. The crude residue was purified by column chromatography (silica, 100-200 mesh, 5% EtOAc in petroleum ether) to afford the title compound (398 g, 51%). $\delta_H$ (400 MHz, DMSO-$d_6$) 8.24-8.20 (m, 1H), 8.01-7.94 (m, 1H), 7.52-7.48 (m, 1H), 2.68 (d, J 1.2 Hz, 3H), 1.19 (s, 9H).

Intermediate 2

(2R)-2-(2-Fluoro-3-nitrophenyl)-2-{[(R)-tert-butyl-sulfinyl]amino}-N-[(4-methoxyphenyl)-methyl]-N-methylpropane-1-sulfonamide n-Butyllithium (85 g, 1.33 mmol) was added at −78° C. under $N_2$ into a solution of N-[(4-methoxyphenyl)methyl]-N-(methyl)methanesulfonamide (WO 2014/093190) (170 g, 0.74 mol) in anhydrous THF (2 L). The reaction mixture was stirred for 2 h, then Intermediate 1 (190 g, 0.66 mol) in anhydrous THF (0.5 L) was slowly added, with stirring for 3 h. The reaction mixture was quenched by the addition of aqueous $NH_4Cl$ solution (500 mL) at 15° C., and extracted with EtOAc (2.5 L). The combined organic layer was washed with brine (500 mL) and concentrated under reduced pressure. The residue was purified by column chromatography ($SiO_2$, petroleum ether/ethyl acetate 50:1 to 2:1) to give the title compound (128 g, 32%) as a yellow oil. $\delta_H$ (400 MHz, DMSO-$d_6$) 8.12-8.09 (m, 1H), 7.98-7.94 (m, 1H), 7.49-7.45 (m, 1H), 7.20-7.18 (d, J 8.4 Hz, 2H), 6.92-6.90 (d, J 8.4 Hz, 2H), 5.65 (s, 1H), 4.08 (s, 2H), 3.86 (s, 2H), 3.73 (s, 3H), 2.56 (s, 3H), 1.98 (s, 3H), 1.16 (s, 9H).

Intermediate 3

(2R)-2-Amino-2-(2-fluoro-3-nitrophenyl)-N-methylpropane-1-sulfonamide

A solution of Intermediate 2 (128 g, 0.24 mol) in HCl/EtOAc (4M, 300 mL) was stirred for 2.5 h at 20-25° C. The crude material was concentrated under vacuum and the residue was dissolved in dichloromethane (220 mL). TFA (554 g, 4.86 mol) in 1,3-dimethoxybenzene (160 mL) was added, then the mixture was warmed to 50-65° C. and stirred for 50 h. The reaction mixture was concentrated under reduced pressure, then the residue was diluted with 1M HCl (600 mL) and extracted with EtOAc (3×1 L). The combined organic layer was re-extracted with 1M HCl (200 mL). The aqueous layer was combined and adjusted to approximately pH 10 with $Na_2CO_3$, then extracted with DCM (2×1 L) and concentrated under reduced pressure, to give the title compound (50 g, 63%) as a yellow oil. $\delta_H$ (400 MHz, DMSO-$d_6$) 8.06-8.02 (m, 1H), 8.00-7.96 (m, 1H), 7.38 (m, 1H), 6.88 (s, 1H), 3.68-3.65 (d, J 14 Hz, 1H), 3.45-3.42 (d, J 14.8 Hz, 1H), 3.15 (s, 3H), 2.56 (s, 2H), 1.48 (s, 3H).

Intermediate 4

(5R)-5-(2-Fluoro-3-nitrophenyl)-3-imino-2,5-dimethyl-1,2,4-thiadiazinane 1,1-dioxide Cyanogen bromide (33.09 g, 0.312 mol) was added to a solution of Intermediate 3 (50.00 g, 0.17 mol) in acetonitrile (750.0 mL) at 20-25° C. The reaction mixture was warmed to 90-100° C. and stirred for 36 h (note: white solid precipitate appeared). The mixture was filtered and the cake was washed with acetonitrile (50 mL). The solid was partitioned between EtOAc (250 mL) and saturated aqueous $Na_2CO_3$ solution (300 mL), then the aqueous layer was extracted with EtOAc (2×250 mL). The combined organic layer was concentrated under reduced pressure to give the title compound (35 g, 64%) as a white solid. $\delta_H$ (400 MHz, DMSO-$d_6$) 7.99-7.96 (m, 1H), 7.88-7.85 (m, 1H), 7.38-7.34 (m, 1H), 6.12 (s, 2H), 3.89-3.78 (m, 2H), 3.01 (s, 3H), 1.58 (s, 3H).

Intermediate 5 tert-Butyl (NE)-N-[(5R)-5-(2-fluoro-3-nitrophenyl)-2,5-dimethyl-1,1-dioxo-1,2,4-thiadiazinan-3-ylidene] carbamate Triethylamine (18.00 mL, 0.12 mol) was added to Intermediate 4 (35 g, 0.11 mol) in DCM (200 mL) at 20-25° C., followed by di-tert-butyl dicarbonate (29.95 g, 0.137 mol). The reaction mixture was stirred for 12 h, then quenched with water (100 mL). The organic phase was separated and washed with saturated aqueous $Na_2CO_3$ solution (100 mL). The organic phase was separated and concentrated under reduced pressure. The residue was purified by column chromatography ($SiO_2$, petroleum ether/ethyl acetate 30:1 to 3:1) to give the title compound (40 g, 82%) as a white solid. $\delta_H$ (400 MHz, DMSO-$d_6$) 8.09-8.06 (m, 1H), 7.66-7.63 (m, 1H), 7.47-7.43 (m, 1H), 4.62-4.59 (d, J 14.4 Hz, 2H), 4.40-4.36 (d, J 14.8 Hz, 1H), 2.99 (s, 3H), 1.81 (s, 3H), 1.41 (s, 9H).

Intermediate 6 tert-Butyl (NE)-N-[(5R)-5-(3-amino-2-fluorophenyl)-2,5-dimethyl-1,1-dioxo-1,2,4-thiadiazinan-3-ylidene]carbamate Pd—C (4.03 g) was added to a solution of Intermediate 5 (40.0 g, 0.11 mol) in MeOH (300.0 mL) and the mixture was purged with $N_2$ three times. The suspension was degassed under vacuum and purged with $H_2$ three times. The reaction mixture was stirred under $H_2$ (30 psi) at 30° C. for 4 h, then filtered. The filter cake was washed with MeOH (50 mL), then the filtrate was concentrated. The crude residue was purified by recrystallization with EtOAc (60 mL) and petroleum ether (600 mL) to give the title compound (25.70 g, 68%) as white solid. $\delta_H$ (400 MHz, DMSO-$d_6$) 6.88-6.84 (m, 1H), 6.76-6.72 (m, 1H), 6.37-6.33 (t, 1H), 5.24 (s, 2H), 4.39-4.31 (m, 2H), 3.02 (s, 3H), 1.77 (s, 3H), 1.43 (s, 9H).

Intermediate 7 tert-Butyl (NE)-N-{(5R)-5-[3-(5-chloro-2-nitroanilino)-2-fluorophenyl]-2,5-dimethyl-1,1-dioxo-1,2,4-thiadiazinan-3-ylidene}carbamate To a solution of Intermediate 6 (0.30 g, 0.77 mmol) in dry THF (10 mL) was added 1.7M tert-butyllithium solution (2.3 mL, 3.88 mmol) dropwise at −78° C. The reaction mixture was stirred at −78° C. for 1 h, followed by the addition of 4-chloro-2-fluoro-1-nitrobenzene (0.13 g, 0.77 mmol) in dry THF (5 mL) at −78° C. The reaction mixture was stirred at room temperature for 16 h, then quenched with brine (100 mL) and extracted with EtOAc (2×100 mL). The organic layer was separated, and washed with H$_2$O (100 mL) and brine (100 mL), then dried over anhydrous Na$_2$SO$_4$ and concentrated in vacuo. The crude residue was purified by column chromatography (silica, 100-200 mesh, 30% EtOAc in hexanes) to afford the title compound (0.29 g, 69%) as a yellow solid. δ$_H$ (400 MHz, CDCl$_3$) 1.57 (s, 9H), 1.92 (s, 3H), 3.26 (s, 3H), 3.69 (d, J 14.2 Hz, 1H), 4.38 (d, J 14.0 Hz, 1H), 6.83 (dd, J 9.1, 2.0 Hz, 1H), 7.04 (s, 1H), 7.22-7.30 (m, 2H), 7.43 (t, J 6.9 Hz, 1H), 8.19 (d, J 9.1 Hz, 1H), 9.37 (s, 1H), 10.69 (s, 1H). LCMS (Method 1, ES+) 542 [M+1]$^+$, 3.88 minutes.

Intermediate 8 tert-Butyl (R,E)-(5-{3-[(2-amino-5-chlorophenyl)amino]-2-fluorophenyl}-2,5-dimethyl-1,1-dioxo-1,2,4-thiadiazinan-3-ylidene)carbamate To a solution of Intermediate 7 (0.26 g, 0.48 mmol) in MeOH (10 mL) were added ammonium formate (0.09 g, 1.44 mmol) and Zn (0.09 g, 1.44 mmol) at 0° C. The reaction mixture was stirred at room temperature for 1 h, then diluted with H$_2$O (100 mL) and extracted with EtOAc (2×50 mL). The organic layer was separated, washed with H$_2$O (100 mL) and brine (100 mL) and concentrated in vacuo to afford the title compound (0.19 g crude) as a yellow solid that was utilised without further purification. δ$_H$ (400 MHz, CDCl$_3$) 1.58 (s, 9H), 1.93 (s, 3H), 3.24 (s, 3H), 3.73 (d, J 13.8 Hz, 1H), 3.78 (s, 2H), 4.31 (d, J 13.8 Hz, 1H), 5.39 (d, J 2.8 Hz, 1H), 6.68-6.78 (m, 3H), 6.92-7.05 (m, 2H), 7.11 (s, 1H), 10.58 (s, 1H). LCMS (Method 1, ES+) 512 [M+1]$^+$, 3.67 minutes.

Intermediate 9 tert-Butyl {(5R,E)-5-[3-(6-chloro-2-methyl-1H-benzo[d]imidazol-1-yl)-2-fluorophenyl]-2,5-dimethyl-1,1-dioxo-1,2,4-thiadiazinan-3-ylidene)carbamate To a solution of Intermediate 8 (0.19 g, 0.37 mmol) in EtOH (12 mL) were added copper(II) acetate (0.13 g, 0.74 mmol) and acetaldehyde (0.30 mL). The reaction mixture was heated at 80° C. for 2 h, then concentrated in vacuo. The residue was dissolved in EtOAc (200 mL), and washed with H$_2$O (100 mL) and brine (100 mL), then dried over anhydrous Na$_2$SO$_4$ and concentrated in vacuo. The crude residue was purified by column chromatography (silica 100-200 mesh, 70% EtOAc in hexanes) to afford the title compound (0.14 g, 71%) as a pale brown solid. δ$_H$ (400 MHz, CDCl$_3$) 1.58 (s, 9H), 1.92 (d, J 6.6 Hz, 3H), 2.43 (s, 3H), 3.22 (s, 3H), 3.62-3.72 (m, 1H), 4.30-4.42 (m, 1H), 7.02 (d, J 15.0 Hz, 1H), 7.46 (m, 4H), 7.67 (s, 1H), 10.70 (s, 1H). LCMS (Method 1, ES+) 532 [M+1]$^+$, 3.48 minutes.

Intermediate 10

1-Chloro-3-fluoro-4-nitro-2-(trifluoromethyl)benzene and 2-Chloro-4-fluoro-1-nitro-3-(trifluoromethyl)benzene To a solution of conc. H$_2$SO$_4$ (3 mL) and conc. HNO$_3$ (3 mL) was added 1-chloro-3-fluoro-2-(trifluoromethyl)benzene (1.00 g, 5.05 mmol) at 0° C. The reaction mixture was stirred at 0° C. for 30 minutes and at room temperature for 2 h, then poured into ice cold H$_2$O (50 mL) and extracted with EtOAc (2×50 mL). The organic layer was washed with H$_2$O (100 mL) and brine (100 mL). The organic layer was separated, dried over anhydrous Na$_2$SO$_4$ and concentrated in vacuo. The crude residue was purified by column chromatography (silica, 100-200 mesh, 20% EtOAc in hexanes) to afford the title compounds (mixture of isomers; 1.00 g, 82%) as a yellow liquid. δ$_H$ (400 MHz, CDCl$_3$; mixture of isomers) 7.21-7.40 (m, 1H), 7.51 (d, J 8.80 Hz, 1H), 7.95 (d, J 3.42 Hz, 1H), 8.17 (br s, 1H).

Intermediate 11 tert-Butyl (NE)-N-[(5R)-5-{3-[3-chloro-6-nitro-2-(trifluoromethyl)anilino]-2-fluorophenyl}-2,5-dimethyl-1,1-dioxo-1,2,4-thiadiazinan-3-ylidene]carbamate To a solution of Intermediate 6 (0.25 g, 0.64 mmol) and Intermediate 10 (as a mixture of isomers) (0.78 g, 3.23 mmol) in THF (12 mL) was added 1.8M tert-butyllithium solution (1.90 mL, 3.23 mmol) dropwise at −78° C. The reaction mixture was stirred at −78° C. for 30 minutes and at room temperature for 16 h, then quenched with brine (100 mL) and extracted with EtOAc (2×50 mL). The organic layer was separated, and washed with H$_2$O (100 mL) and brine (100 mL), then dried over anhydrous Na$_2$SO$_4$ and concentrated in vacuo. The crude residue was purified by column chromatography (silica, 100-200 mesh, 30% EtOAc in hexanes) to afford the title compound (80% purity by LCMS) (0.12 g, 30%) as a yellow solid. δ$_H$ (400 MHz, CDCl$_3$) 1.58 (m, 9H), 1.92 (s, 3H), 3.25 (s, 3H), 3.72 (d, J 14.1 Hz, 1H), 4.22 (d, J 14.1 Hz, 1H), 6.81 (t, J 7.9 Hz, 1H), 6.94-7.08 (m, 2H), 7.36 (d, J 8.9 Hz, 1H), 7.95 (s, 1H), 8.13 (d, J 8.9 Hz, 1H), 10.62 (s, 1H). LCMS (Method 1, ES+) 594 [M+1]$^+$, 3.81 minutes.

Intermediate 12 tert-Butyl (NE)-N-[(5R)-5-{3-[6-amino-3-chloro-2-(trifluoromethyl)anilino]-2-fluorophenyl}-2,5-dimethyl-1,1-dioxo-1,2,4-thiadiazinan-3-ylidene]carbamate To a solution of Intermediate 11 (0.12 g, 0.19 mmol) in MeOH (6 mL) were added ammonium formate (0.04 g, 0.59 mmol) and Zn (0.04 g, 0.59 mmol) at 0° C. The reaction mixture was stirred at 0° C. for 15 minutes and at room temperature for 15 minutes, then diluted with H$_2$O (50 mL) and extracted with EtOAc (2×50 mL). The organic layer was separated, and washed with H$_2$O (100 mL) and brine (100 mL), then concentrated in vacuo, to afford the title compound in 80% purity (0.10 g, crude) as a yellow solid that was utilised without further purification. LCMS (Method 1, ES+) 580 [M+1]+, 3.77 minutes.

Intermediate 13 tert-Butyl (5R,E)-(5-{3-[6-chloro-2-methyl-7-(trifluoromethyl)-1H-benzo[d]imidazol-1-yl]-2-fluorophenyl}-2,5-dimethyl-1,1-dioxo-1,2,4-thiadiazinan-3-ylidene)carbamate To a solution of Intermediate 12 (0.10 g, 0.17 mmol) in EtOH (10 mL) were added copper(II) acetate (0.06 g, 0.34 mmol) and acetaldehyde (0.20 mL). The reaction mixture was heated at 80° C. for 1 h, then concentrated in vacuo. The residue was dissolved in EtOAc (100 mL), and washed with H$_2$O (100 mL) and brine (100 mL), then dried over anhydrous Na$_2$SO$_4$ and concentrated in vacuo. The crude residue was purified by column chromatography (silica, 100-200 mesh, 70% EtOAc in hexanes) to afford the title compound in 80% purity (0.03 g, 29%) as a pale brown solid. LCMS (Method 1, ES+) 550 [M+1]+, 3.93 minutes.

Intermediate 14

(E)-2-(4-Chlorophenyl)-3-{2-fluoro-3-[(5R)-3-imino-2,5-dimethyl-1,1-dioxo-1,2,4-thiadiazinan-5-yl]aniline}but-2-enenitrile To a solution of Intermediate 6 (0.30 g, 0.77 mmol) in acetic acid (3 mL) was added 2-(4-chlorophenyl)-3-oxobutanenitrile (0.18 g, 0.93 mmol). The reaction mixture was heated under microwave irradiation at 130° C. for 45 minutes, then concentrated in vacuo. The residue was dissolved in EtOAc (100 mL), then filtered through Celite. The filtrate was concentrated in vacuo to afford the title compound (0.32 g crude) as a white semi-solid. LCMS (Method 1, ESI) 462.00 [M+1]+, 2.92 minutes.

Intermediate 15 tert-Butyl (NZ)—N-[(5R)-5-{3-[6-chloro-2-(dimethylamino)benzimidazol-1-yl]-2-fluorophenyl}-2,5-dimethyl-1,1-dioxo-1,2,4-thiadiazinan-3-ylidene]carbamate To a solution of Intermediate 8 (0.30 g, 0.58 mmol) in DCM (12 mL) was added (dichloromethylene)dimethylammonium chloride (0.19 g, 1.17 mmol). The reaction mixture was stirred at room temperature for 5 h, then diluted with water (80 mL) and extracted with DCM (2×50 mL). The organic layer was washed with water (100 mL), saturated aqueous NaHCO$_3$ solution (100 mL) and brine (100 mL). The organic layer was separated, dried over anhydrous Na$_2$SO$_4$ and concentrated in vacuo. The crude residue was purified by column chromatography (silica, 100-200 mesh, 60% EtOAc in hexanes) to afford the title compound as an off-white solid. δ$_H$ (400 MHz, CDCl$_3$) 1.58 (s, 9H), 1.94 (s, 3H), 2.87 (s, 6H), 3.25 (s, 3H), 3.66 (d, J 14.4 Hz, 1H), 4.41 (d, J 14.0 Hz, 1H), 6.73 (s, 1H), 7.15 (d, J 8.40 Hz, 1H), 7.38-7.49 (m, 4H), 10.75 (s, 1H). LCMS (Method 1, ESI) 565.00 [M+1]+, 3.48 minutes.

Intermediate 16 tert-Butyl (NE)-N-{(5R)-5-[3-(6-chloro-2-oxo-3H-benzimidazol-1-yl)-2-fluorophenyl]-2,5-dimethyl-1,1-dioxo-1,2,4-thiadiazinan-3-ylidene}carbamate To a solution of Intermediate 8 (0.80 g, 1.56 mmol) in THF (50 mL) were added triethylamine (0.43 g, 3.12 mmol) and triphosgene (0.55 g, 1.87 mmol) at 0° C. The reaction mixture was stirred at room temperature for 2 h, then quenched with water (50 mL) and extracted with EtOAc (2×50 mL). The organic layer was separated and washed with brine (50 mL), then dried over anhydrous Na$_2$SO$_4$ and concentrated in vacuo. The crude residue was purified by column chromatography (silica, 100-200 mesh, 50% EtOAc in hexanes) to afford the title compound (0.60 g, 71%) as an off-white solid. δ$_H$ (400 MHz, CDCl$_3$) 1.58 (s, 9H), 1.91 (s, 3H), 3.25 (s, 3H), 3.69 (d, J 14.4 Hz, 1H), 4.47 (d, J 14.0 Hz, 1H), 6.91 (s, 1H), 7.04 (d, J 8.40 Hz, 1H), 7.13 (d, J 8.40 Hz, 1H), 7.37-7.41 (m, 2H), 7.53-7.56 (m, 1H), 8.85 (s, 1H) 10.69 (s, 1H). LCMS (Method 1, ESI) 538.00 [M+1]+, 1.95 minutes.

Intermediate 17

(5R)-5-[3-(2,6-Dichlorobenzimidazol-1-yl)-2-fluorophenyl]-2,5-dimethyl-1,1-dioxo-1,2,4-thiadiazinan-3-imine A stirred solution of Intermediate 16 (0.50 g, 0.92 mmol) in POCl$_3$ (8 mL) was heated at 120° C. for 8 h, after which time the reaction mixture was concentrated in vacuo. The residue was quenched with ice and aqueous NaHCO$_3$ solution (50 mL), then extracted with EtOAc (4×100 mL). The organic layer was separated and dried over anhydrous Na$_2$SO$_4$, then concentrated in vacuo, to afford the title compound as an off-white solid, which was utilised without further purification. LCMS (Method 1, ESI) 456.00 [M+1]+, 1.79 minutes.

Intermediate 18 tert-Butyl (NE)-N-[(5R)-5-{3-[6-chloro-2-(morpholin-4-yl)benzimidazol-1-yl]-2-fluorophenyl}-2,5-dimethyl-1,1-dioxo-1,2,4-thiadiazinan-3-ylidene]carbamate To a solution of Intermediate 8 (0.25 g, 0.48 mmol) in DCM (20 mL) was added 4-(dichloromethylene)morpholin-4-ium chloride (0.10 g, 0.48 mmol) at 0° C. The reaction mixture was stirred at room temperature for 2 h, then quenched with water (10 mL) and extracted with EtOAc (3×20 mL). The organic layer was separated and washed with brine (20 mL), then dried over anhydrous Na$_2$SO$_4$ and concentrated in vacuo. The crude residue was purified by column chromatography (silica, 100-200 mesh, EtOAc) to afford the title compound (0.20 g, 68%) as an off-white solid. LCMS (Method 1, ESI) 607.00 [M+1]+, 2.07 minutes.

Intermediate 19 tert-Butyl (NE)-N-[(5R)-5-{2-fluoro-3-[3-fluoro-6-nitro-2-(trifluoromethyl)anilino]-phenyl}-2,5-dimethyl-1,1-dioxo-1,2,4-thiadiazinan-3-ylidene]carbamate To a solution of Intermediate 6 (1.00 g, 2.58 mmol) in THF (56 mL) was added tert-butyllithium (6.60 mL, 7.74 mmol) dropwise at −78° C. and the reaction mixture was stirred at −78° C. for 1 h. 1,3-Difluoro-4-nitro-2-(trifluoromethyl)benzene (0.58 g, 2.58 mmol) was added at −78° C. and the reaction mixture was stirred at room temperature for 5 h, then quenched with brine (200 mL) and extracted with EtOAc (2×100 mL). The organic layer was separated, washed with water (100 mL) and brine (100 mL), then dried over anhydrous $Na_2SO_4$ and concentrated in vacuo. The crude residue was purified by column chromatography (silica, 100-200 mesh, 30% EtOAc in hexanes) to afford the title compound (0.55 g, 36%) as a yellow solid. $\delta_H$ (400 MHz, $CDCl_3$) 1.54 (s, 9H), 1.92 (s, 3H), 3.25 (s, 3H), 3.71 (d, J 14.0 Hz, 1H), 4.22 (d, J 13.2 Hz, 1H), 6.86-6.90 (m, 1H), 6.98-7.03 (m, 3H), 8.05 (m, 1H), 8.27-8.31 (m, 1H), 10.62 (s, 1H). LCMS (Method 1, ESI) 594.00 $[M+1]^+$, 3.61 minutes.

Intermediate 20 tert-Butyl (NE)-N-[(5R)-5-{3-[6-amino-3-fluoro-2-(trifluoromethyl)anilino]-2-fluorophenyl}-2,5-dimethyl-1,1-dioxo-1,2,4-thiadiazinan-3-ylidene]carbamate To a solution of Intermediate 19 (0.55 g, 0.92 mmol) in MeOH (15 mL) were added ammonium formate (0.17 g, 2.78 mmol) and Zn dust (0.18 g, 2.78 mmol) at 0° C. The reaction mixture was stirred at room temperature for 1 h, then diluted with water (100 mL) and extracted with EtOAc (2×100 mL). The organic layer was separated and washed with water (100 mL), then dried over anhydrous $Na_2SO_4$ and concentrated in vacuo, to afford the title compound (0.45 g crude) as a brown solid, which was utilised without further purification. LCMS (Method 1, ESI) 564.00 $[M+1]^+$, 3.55 minutes.

Intermediate 21 tert-Butyl (NE)-N-[(5R)-5-{2-fluoro-3-[6-fluoro-2-methyl-7-(trifluoromethyl)-benzimidazol-1-yl]phenyl}-2,5-dimethyl-1,1-dioxo-1,2,4-thiadiazinan-3-ylidene]-carbamate To a solution of Intermediate 20 (0.45 g, 0.79 mmol) in EtOH (20 mL) were added copper(II) acetate (0.28 g, 1.59 mmol) and acetaldehyde (0.60 mL). The reaction mixture was heated at 80° C. for 2 h, then concentrated in vacuo. The residue was dissolved in EtOAc (150 mL), then washed with water (50 mL) and brine (100 ml). The organic layer was separated, dried over anhydrous $Na_2SO_4$ and concentrated in vacuo. The crude residue was purified by column chromatography (silica, 100-200 mesh, 60% EtOAc in hexanes) to afford the title compound (0.13 g, 29%) as a brown solid. LCMS (Method 1, ESI) 488.00 $[M+1]^+$, 2.40 minutes.

Example 1

(5R)-5-[3-(6-Chloro-2-methyl-1H-benzo[d]imidazol-1-yl)-2-fluorophenyl]-3-imino-2,5-dimethyl-1,2,4-thiadiazinane 1,1-dioxide To a solution of Intermediate 9 (0.14 g, 0.27 mmol) in DCM (6 mL) was added TFA (0.4 mL) at 0° C. The reaction mixture was stirred at room temperature for 5 h, then concentrated in vacuo. The crude residue was washed with diethyl ether (50 mL), then lyophilised and dried in vacuo, to afford the title compound, TFA salt (0.07 g, 59%) as a pale brown solid. $\delta_H$ (400 MHz, DMSO-$d_6$) 1.85 (d, J 2.80 Hz, 1H), 2.34 (s, 3H), 2.41 (s, 3H), 2.94 (d, J 4.00 Hz, 3H), 4.54-4.59 (m, 1H), 4.74-4.80 (m, 1H), 5.30-5.50 (m, 2H), 7.28 (d, J 8.80 Hz, 1H), 7.51-7.60 (m, 1H), 7.67 (d, J 8.80 Hz, 1H), 7.73-7.78 (m, 1H), 10.66 (d, J 9.60 Hz, 1H). LCMS (Method 1, ES+) 436 $[M+1]^+$, 1.80 minutes.

Example 2

(5R)-5-{3-[6-Chloro-2-methyl-7-(trifluoromethyl)-1H-benzo[d]imidazol-1-yl]-2-fluorophenyl}-3-imino-2,5-dimethyl-1,2,4-thiadiazinane 1,1-dioxide To a solution of Intermediate 13 (0.030 g, 0.049 mmol) in DCM (3 mL) was added TFA (0.1 mL) at 0° C. The reaction mixture was stirred at room temperature for 5 h, then concentrated in vacuo. The residue was washed with diethyl ether (50 mL), then lyophilised and dried in vacuo, to afford the title compound, TFA salt, in 77% purity (25 mg, crude). LCMS (Method 1, ES+) 504 $[M+1]^+$, 2.20 minutes.

Example 3

6-Chloro-1-{2-fluoro-3-[(5R)-3-imino-2,5-dimethyl-1,1-dioxo-1,2,4-thiadiazinan-5-yl]-phenyl}-2-methylindole-3-carbonitrile To a solution of Intermediate 14 (0.32 g, 0.69 mmol) in DCM (6 mL) was added a solution of [bis(trifluoroacetoxy)iodo]benzene (0.33 g, 0.77 mmol) in DCM (2 mL) dropwise at 0° C. The reaction mixture was stirred at room temperature for 16 h, then concentrated in vacuo. The crude residue was purified by column chromatography (silica, 100-200 mesh, 5% MeOH in DCM) and preparative HPLC to afford the title compound (0.058 g, 16%, mixture of atropisomers) as an off-white solid. LCMS (Method 1, ESI) 460.00 $[M+1]^+$, 2.40 minutes.

Example 4

6-Chloro-1-{2-fluoro-3-[(5R)-3-imino-2,5-dimethyl-1,1-dioxo-1,2,4-thiadiazinan-5-yl]-phenyl}-N,N-dimethylbenzimidazol-2-amine To a solution of Intermediate 15 (0.14 g, 0.24 mmol) in DCM (8 mL) was added TFA (0.4 mL) at 0° C. The reaction mixture was stirred at room temperature for 4 h, then concentrated in vacuo. The crude residue was washed with diethyl ether (20 mL) and hexane (20 mL) to afford the title compound (TFA salt) (0.10 g, 87%, mixture of atropisomers) as an off-white solid. $\delta_H$ (400 MHz, DMSO-$d_6$) 1.86 (s, 3H), 2.85 (s, 3H), 2.86 (s, 3H), 3.19 (s, 3H), 4.72 (d, J 14.8 Hz, 1H), 4.84 (d, J 14.8 Hz, 1H), 6.80 (s, 1H), 6.93 (s, 1H), 7.20-7.28 (m, 1H), 7.42 (d, J 8.40 Hz, 1H), 7.51-7.58 (m, 1H), 7.72-7.82 (m, 1H), 8.91 (s, 1H), 10.80 (s, 1H). LCMS (Method 1, ESI) 465.00 $[M+1]^+$, 1.48 minutes.

Example 5

(5R)-5-{3-[6-Chloro-2-(pyrrolidin-1-yl)benzimidazol-1-yl]-2-fluorophenyl}-2,5-dimethyl-1,1-dioxo-1,2,4-thiadiazinan-3-imine To a solution of Intermediate 17 (0.40 g, 0.87 mmol) in isopropanol (5 mL) was added pyrrolidine (0.62 g, 8.79 mmol). The reaction mixture was heated at 90° C. for 16 h, then concentrated in vacuo. The crude residue was purified by preparative HPLC to afford the title compound (0.025 g, 6%, mixture of atropisomers) as an off-white solid. LCMS (Method 1, ESI) 491.00 [M+1]$^+$, 2.21 minutes.

Example 6

(5R)-5-{3-[6-Chloro-2-(morpholin-4-yl)benzimidazol-1-yl]-2-fluorophenyl}-2,5-dimethyl-1,1-dioxo-1,2,4-thiadiazinan-3-imine To a solution of Intermediate 18 (0.20 g, 0.32 mmol) in DCM (10 mL) was added TFA (0.18 g, 1.65 mmol) at 0° C. The reaction mixture was stirred at room temperature for 3 h, then concentrated in vacuo. The crude residue was purified by preparative HPLC to afford the title compound (TFA salt) (0.135 g, 66%, mixture of atropisomers) as an off-white solid. LCMS (Method 1, ESI) 507.00 [M+1]$^+$, 2.38 minutes.

Example 7

(5R)-5-{2-Fluoro-3-[6-fluoro-2-methyl-7-(trifluoromethyl)benzimidazol-1-yl]phenyl}-2,5-dimethyl-1,1-dioxo-1,2,4-thiadiazinan-3-imine To a solution of Intermediate 21 (0.13 g, 0.22 mmol) in DCM (12 mL) was added TFA (0.6 mL) at 0° C. The reaction mixture was stirred at room temperature for 6 h, then concentrated in vacuo. The crude residue was washed with diethyl ether:hexane (2:8, 40 mL) to afford the title compound (TFA salt) (0.09 g, 84%, mixture of atropisomers) as a brown solid. LCMS (Method 1, ESI) 488.00 [M+1]+, 2.40 and 2.41 minutes.

The invention claimed is:

1. A compound represented by formula (IIA), or a pharmaceutically acceptable salt thereof:

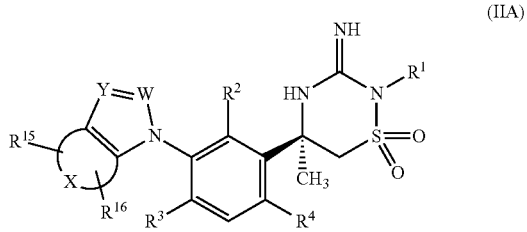

(IIA)

wherein
X represents the residue of a benzene or pyridine ring;
W represents N or C—R$^{13}$;
Y represents N or C—R$^{14}$;
R$^1$ represents C$_{1-6}$ alkyl;
R$^2$ and R$^3$ independently represent hydrogen or halogen;
R$^4$ represents hydrogen;
R$^{13}$ represents hydrogen, methyl, ethyl, hydroxymethyl, 1-hydroxyethyl, dimethylamino, pyrrolidinyl or morpholinyl;
R$^{14}$ represents cyano;
R$^{15}$ and R$^{16}$ independently represent hydrogen, halogen, cyano, nitro, C$_{1-6}$ alkyl, trifluoromethyl, methylpyrazolyl, hydroxy, hydroxy(C$_{1-6}$)alkyl, C$_{1-6}$ alkoxy, difluoro-methoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, C$_{2-6}$ alkylcarbonylamino, C$_{2-6}$ alkoxycarbonylamino, C$_{1-6}$ alkylsulfonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$) alkylaminocarbonyl, aminosulfonyl, C$_{1-6}$ alkylaminosulfonyl or di(C$_{1-6}$)alkylaminosulfonyl.

2. The compound as claimed in claim 1 represented by formula (IIA-1a), or a pharmaceutically acceptable salt thereof:

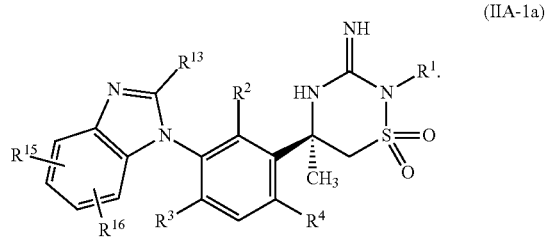

(IIA-1a)

3. The compound as claimed in claim 1 represented by formula (IIA-2a), or a pharmaceutically acceptable salt thereof:

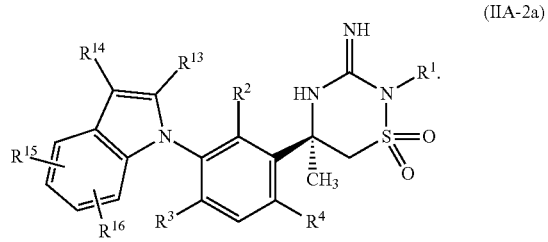

(IIA-2a)

4. The compound as claimed in claim 1 selected from,
(5R)-5-[3-(6-Chloro-2-methyl-1H-benzo[d]imidazol-1-yl)-2-fluorophenyl]-3-imino-2,5-dimethyl-1,2,4-thiadiazinane 1,1-dioxide,
(5R)-5-{3-[6-Chloro-2-methyl-7-(trifluoromethyl)-1H-benzo[d]imidazol-1 -yl]-2-fluoro-phenyl}-3-imino-2,5-dimethyl-1,2,4-thiadiazinane 1,1-dioxide,
6-Chloro-1-{2-fluoro-3-[(5R)-3-imino-2,5-dimethyl-1,1-dioxo-1,2,4-thiadiazinan-5-yl]-phenyl}-2-methylindole-3-carbonitrile,
6-Chloro-1-{2-fluoro-3-[(5R)-3-imino-2,5-dimethyl-1,1-dioxo-1,2,4-thiadiazinan-5-yl]-phenyl}-N,N-dimethyl-benzimidazol-2-amine,
(5R)-5-{3-[6-Chloro-2-(pyrrolidin-1-yl)benzimidazol-1-yl]-2-fluorophenyl}-2,5-dimethyl-1,1-dioxo-1,2,4-thiadiazinan-3-imine,
(5R)-5-{3[6-Chloro-2-(morpholin-4-yl)benzimidazol-1-yl]-2-fluorophenyl}-2,5-dimethyl-1,1-dioxo-1,2,4-thiadiazinan-3-imine, and
(5R)-5-{2-Fluoro-3-[6-fluoro-2-methyl-7-(trifluoromethyl)benzimidazol-1-yl]phenyl}-2,5-dimethyl-1,1-dioxo-1,2,4-thiadiazinan-3-imine.

5. A pharmaceutical composition comprising a compound of formula (IIA) as defined in claim 1 or a pharmaceutically acceptable salt thereof in association with a pharmaceutically acceptable carrier.

6. A method for the treatment of malaria, which comprises administering to a patient in need of such treatment an effective amount of a compound of formula (IIA) as defined in claim 1 or a pharmaceutically acceptable salt thereof.

7. The compound as claimed in claim 1 wherein R$^1$ represents methyl.

8. The compound as claimed in claim 1 wherein $R^2$ represents fluoro.

9. The compound as claimed in claim 7 wherein $R^2$ represents fluoro.

10. The compound as claimed in claim 2 wherein $R^1$ represents methyl.

11. The compound as claimed in claim 2 wherein $R^2$ represents fluoro.

12. The compound as claimed in claim 10 wherein $R^2$ represents fluoro.

13. The compound as claimed in claim 3 wherein $R^1$ represents methyl.

14. The compound as claimed in claim 3 wherein $R^2$ represents fluoro.

15. The compound as claimed in claim 13 wherein $R^2$ represents fluoro.

* * * * *